(12) United States Patent
Aronson et al.

(10) Patent No.: US 6,265,368 B1
(45) Date of Patent: *Jul. 24, 2001

(54) AQUEOUS DETERGENT COMPOSITIONS THICKENED USING CARRAGEENAN

(75) Inventors: Michael Paul Aronson, Edgewater, NJ (US); Charles Rupert Brown, Bedford (GB); Robert James Chatfield, Bebington (GB); Edwin Willis, Church Stretton (GB)

(73) Assignee: Lever Brothers Company, division of Conopco, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/252,711

(22) Filed: Feb. 18, 1999

(30) Foreign Application Priority Data

Feb. 23, 1998 (GB) .................................................. 9803770

(51) Int. Cl.[7] ........................................................ C11D 3/38
(52) U.S. Cl. ........................ 510/403; 510/121; 510/140; 510/158; 510/470
(58) Field of Search .................................. 510/470, 403, 510/121, 140, 158; 252/FOR 239

(56) References Cited

U.S. PATENT DOCUMENTS

| 4,474,818 | * | 10/1984 | Scott | 514/777 |
|---|---|---|---|---|
| 4,543,250 | | 9/1985 | Witt | 424/70.13 |
| 4,738,794 | * | 4/1988 | Harrison et al. | 510/372 |
| 4,774,016 | * | 9/1988 | Gazzani | 510/121 |
| 4,897,214 | * | 1/1990 | Gazzani | 510/119 |
| 5,002,934 | * | 3/1991 | Norton et al. | 514/54 |
| 5,310,508 | * | 5/1994 | Subramanyam et al. | 510/140 |
| 5,534,265 | * | 7/1996 | Fowler et al. | 424/489 |
| 5,538,663 | | 7/1996 | Kihara et al. | 510/395 |
| 5,756,437 | * | 5/1998 | Yamazaki et al. | 510/136 |
| 5,785,979 | * | 7/1998 | Wells | 424/401 |
| 5,798,108 | * | 8/1998 | Nadaud et al. | 510/130 |
| 5,910,472 | * | 6/1999 | Elliott et al. | 510/124 |

FOREIGN PATENT DOCUMENTS

| 11076/92 | | 8/1992 | (AU) . |
|---|---|---|---|
| 0271131 | | 6/1988 | (EP) . |
| 0 355 908 B1 | * | 2/1990 | (EP) . |
| 0355908 | | 2/1990 | (EP) . |
| 0500423 | | 8/1992 | (EP) . |
| 0502895 | | 1/1996 | (EP) . |
| 2188060 | | 9/1987 | (GB) . |
| 2-123193 | * | 5/1990 | (JP) . |
| 8-310942 | * | 11/1996 | (JP) . |
| 9-249527 | * | 9/1997 | (JP) . |
| 91/08283 | | 6/1991 | (WO) . |
| 97/45510 | * | 12/1997 | (WO) . |

OTHER PUBLICATIONS

"Gels and Gelling", Allan H. Clark, Physical Chemistry of Foods, Schwartzenberg & Hartel, Chapter 5, Marcel Dekker, 1992.

"Carrageenans", N. F. Stanley, Food Gels, Chapter 3, Peter Harris, Elsevier, 1990.

* cited by examiner

Primary Examiner—William Krynski
Assistant Examiner—Dawn L. Garrett
(74) Attorney, Agent, or Firm—Ronald A. Koatz

(57) ABSTRACT

A thickened, aqueous detergent composition having an aqueous phase containing foaming surfactant, carrageenan and water. Conveniently, the carrageenan is at least half kappa or iota carrageenan, or a mixture of the two.

14 Claims, No Drawings

AQUEOUS DETERGENT COMPOSITIONS THICKENED USING CARRAGEENAN

This invention relates to detergent compositions for use in personal washing which are in the form of viscous aqueous liquids or soft solids.

A number of detergent products for personal washing are formulated as viscous liquids, creams or gels. Examples of such products are hair shampoos, shower gels and facial washes. Such products generally contain foaming surfactant, which usually comprises at least 3 wt % of anionic surfactant possibly accompanied by amphoteric, zwitterionic or nonionic surfactant. It is conventional for such products to contain one or more ingredients whose function is to increase the viscosity of the composition.

One possibility is to incorporate a sufficient quantity of electrolyte together with a sufficient quantity of selected surfactant, so that the surfactant is present in a viscous phase, and thus increases the viscosity of the resulting composition.

It is also known to incorporate polymeric materials to enhance viscosity. One category of synthetic polymers used for this purpose are crosslinked polyacrylates, for instance those sold under the trademark Carbopol. Natural polymers have also been used for this purpose, and in particular xanthan gum has been used. Personal washing products, especially shampoos, containing xanthan gum are described in, for example, U.S. Pat. No. 5,151,210 and EP 500423. Personal washing products containing other biological polymers have been described, for example in GB-A-2188060.

A number of polymers of natural origin have the ability to increase the viscosity of water in which they are dissolved. A well known example is agar. A aqueous solution containing a small percentage of agar is a mobile liquid when hot, but when left to cool it forms a gel with sufficient rigidity to maintain its own shape.

The formation of gels by natural polysaccharides arises from interaction between the polymer molecules. Above a temperature referred to as the gel point, this interaction largely disappears and the hot solution of polymer is mobile. When it cools below its gel point, the interaction of polymer molecules enables them to form a continuous and branched network which extends throughout the sample. This can be described as a network extending "from wall to wall" of the container holding the sample.

Gel formation by aqueous solutions of natural polymers can lead to a wide range of physical properties. A so-called strong gel is sufficiently rigid that it cannot flow. When a sample is subjected to mechanical stress, it eventually breaks. A so-called weak gel is able to flow, and natural polysaccharides can be used to produce compositions which have the appearance of mobile liquids, albeit thicker than water. In contrast with the formation of a continuous, branched network, some materials which thicken water do so through merely local, transient entanglement of molecules.

A discussion of polysaccharides gels, including their range of mechanical properties, is found in "gels and gelling" by Allan H Clark which is Chapter 5 in Physical Chemistry of Foods, Schwartzberg and Hartel, editors; published by Marcel Dekker 1992.

In the present specification, the expression "thickened aqueous composition" will be used to denote aqueous compositions with any viscosity greater than that of water.

EP-A-271131 discloses a number of products intended for application to skin and thickened with carrageenan gels. Many of these do not include surfactant. One product disclosed in this document is a cleansing composition containing a nonionic surfactant which produces negligible foam.

We have found that foaming surfactants cannot be incorporated into a number of gels formed by naturally occurring polymers. The surfactant makes the gel unstable and phase separation occurs. Xanthan gum can be incorporated as a thickener in aqueous compositions containing surfactant but the resulting products tend to have a stringy texture and a slimy feel which are not liked by users.

By contrast, however, we have now found that thickened viscous aqueous compositions formed with carrageenan do not phase separate with foaming surfactants and can be used to form personal washing compositions which are in the form of viscous liquids or gels and have a good combination of consumer properties.

According to the present invention, therefore, we provide a thickened aqueous detergent composition having an aqueous phase containing foaming surfactant and carrageenan.

Carrageenans are a class of polysaccharides which occur in red seaweeds. They are linear polysaccharides made up from alternating $\beta$-1,3- and $\alpha$-1,4-linked galactose residues. The 1,4-linked residues are the D-enantioner and sometimes occur as the 3,6-anhydride. Many of the galactose residues are sulphated.

A number of carrageenan structures have been described and commercial materials are available which approximate to the ideal structures. However, variations between these structures occur, depending on the source of the carrageenan and treatment of it after extraction.

A description of different carrageenan types is given in "Carrageenans" by Norman F Stanley which is Chapter 3 of "Food Gels" edited by Peter Harris, Elsevier, 1990.

Kappa carrageenan is sulphated on the 1,3-linked galactose residues, but not on the 1,4-linked residues. Iota carrageenan is sulphated on both residues. Lambda carrageenan has two sulphate groups on the 1,4-linked residues and one sulphate group on 70% of the 1,3-linked residues. Industrial treatment of lambda carrageenan with base can remove one sulphate group from some of the 1,4-linked residues: the resulting structure is designated theta carrageenan but does not occur naturally.

Commercially available kappa, iota and lambda carrageenans consist predominantly of material approximating to be ideal structures mentioned above.

Aqueous solutions of kappa and iota carrageenan exist as gels. Lambda carrageenan on its own in aqueous solution does not form gels because its molecular structure prevents association between its molecules and consequent structuring in liquids.

Compositions of this invention contain carrageenan and surfactant in an aqueous phase. The carrageenan increases the viscosity of this phase, and in certain forms of the invention the carrageenan does this by forming a continuous network within this aqueous phase.

Compositions of this invention may be intended for use as personal washing products such as shampoos, shower gels, facial washes, or hand cleansers. For this purpose the composition may consist solely of a thickened continuous aqueous phase or it may incorporate suspended particles of a liquid (eg a water-immiscible oil) or of a solid.

The amount of carrageenan in a composition of the invention may be as low as 0.05% by weight of the aqueous phase of the composition, leading to a mobile, but thickened liquid. The amount may be higher, such as at least 0.1, 0.3 or 0.5% by weight. The amount is unlikely to exceed 5% by weight of the aqueous phase of the composition, preferably not over 4% or 3.5% by weight. A preferred weight range is from 0.5 to 2.5% especially 0.7 to 2.0%.

More than half of the carrageenan may preferably be kappa or iota carrageenan or a mixture of the two. Lambda carrageenan may be used to form thickened liquid compositions which do not contain a continuous network of associated carrageenan molecules, but nevertheless come within the broadest scope of this invention. Also, lambda carrageenan may be used in mixtures with kappa and/or iota carrageenans.

A composition in accordance with this invention may have an appearance resembling a thickened but still mobile, self-levelling liquid. Alternatively, it may have an appearance which is more characteristic of a soft solid. It may be a soft gel, which breaks up easily when disturbed, but retains a lumpy appearance. It may be a firm gel, which can retain its shape during handling, although it can be broken up by application of force. In between, a gel may be elastic so as to distort under its own weight, but retain its shape better than a soft gel.

It will generally be necessary to provide a sufficient quantity of carrageenan to provide ordering within the aqueous phase, and consequent thickening. Further increases in the amount of kappa or iota carrageenan tend to lead to increasing viscosity and/or gel strength, although the changes observed are not always linear increases in viscosity with carrageenan concentration.

If kappa carrageenan is used alone, the compositions obtained are smooth, with viscosity which depends on concentration. Compositions with relatively small concentrations of this carrageenan have the appearance of mobile liquids but stronger gels are produced at higher concentration typically 1.5% by weight or more.

Iota carrageenan tends not to give smoothly pouring compositions, but instead gives soft, lumpy and elastic textures. Rather smaller quantities of iota carrageenan than kappa carrageenan are needed to give similar viscosities. For instance in a test of these carrageenans with 10% by weight of commercial surfactant (a 13:2 mixture of sodium lauryl ether sulphate and a betaine) 0.6% by weight iota carrageenan produced an elastic gel whereas 0.6% by weight kappa carrageenan produced a mobile, although thickened, liquid. It is generally true that increasing the concentration of kappa carrageenan, iota carrageenan or a mixture of them increases viscosity and/or gel strength progressively.

As mentioned, lambda carrageenan does not on its own form a continuous network. Smooth thickened compositions without a continuous network can be obtained using surfactant and concentrations of lambda carrageenan which are large relative to useful concentrations of kappa or iota carrageenan.

Lambda carrageenan can be used jointly with kappa or iota carrageenan whereupon it does contribute to the overall viscosity or gel strength. For instance, 1.4% of kappa carrageenan alone in a composition containing 10% surfactant produced a thick mobile liquid but adding 1.4% lambda carrageenan to this mixture produced a composition in the form of a soft gel which retained a lumpy appearance when an attempt was made to pour it.

The viscosities of compositions containing kappa or iota carrageenan can be modified by incorporating a small amount of electrolyte. Addition of sodium ions, for example as sodium chloride, increases gel strength moderately. Addition of potassium or calcium ions gives a rather greater enhancement of gel strength. Potassium ions are particularly affective to increase viscosity of kappa carrageenan while calcium ions are particularly affective with iota carrageenan.

When selecting carrageenan type, concentration and accompanying electrolyte concentration, the nature of the thickened liquids/gels which are obtained can be investigated by producing a number of trial compositions as exemplified below. Commercial supplies of surfactant will generally contain some electrolyte as impurity and allowance should be made for this, for instance by carrying out trials using commercial surfactant from the source envisaged as supplier for subsequent manufacture. In general, electrolyte comprises 0.1 to 5% by wt. of composition other than whatever is brought in by the surfactant.

Compositions of this invention contain at least 3 wt % of a foaming surfactant system, preferably from 5 wt % up to 30 wt %. Ranges from 7 or 10% up to 15 or 20% are preferred. At least half, better at least two-thirds of all the surfactant present is preferably selected from anionic, amphoteric or zwitterionic surfactants, or nonionic surfactants other than ethoxylated fatty alcohols. Instances of such nonionic surfactants are alkyl glycosides (more specifically alkylpolyglycosides), O-alkanoyl glycosides, polyethylene oxide-polypropylene oxide block copolymers, alkyl polyhydroxyamides (which may be referred to as alkyl glucamides), alkyl aldobionamides (notably including lactobionamides) and their mixtures.

Preferably the composition contains at least 5% anionic surfactant possibly accompanied by amphoteric or zwitterionic surfactant.

Ethoxylated fatty alcohols, which are low-foaming nonionic surfactants, need not be excluded but will generally not exceed half of the surfactant present. Preferably, the amount (if any) of such surfactant is not more than a quarter of the surfactant present.

One type of anionic surfactant which is frequently used in personal washing compositions, and which may be used in compositions of this invention, is alkyl ether sulphate of the formula:

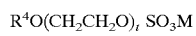

where $R^4$ is alkyl or alkenyl of 8 to 18 carbon atoms, especially 11 to 15 carbon atoms, t has an average value of at least 2.0 and M is a solubilising cation such as sodium, potassium, ammonium or substituted ammonium. Preferably t has an average value of 3 or more.

Other anionic surfactants may be used. Possibilities include alkyl glyceryl ether sulphates, sulphosuccinates, taurates, sarcosinates, acyl isethionates, sulphoacetates, alkyl phosphates and acyl lactates.

Sulphosuccinates may be monoalkyl sulphosuccinates (having the formula:

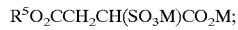

or amido-MEA sulphosuccinates of the formula:

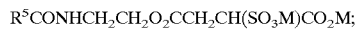

wherein $R^5$ ranges from $C_8$–$C_{20}$ alkyl, preferably $C_{12}$–$C_{15}$ alkyl and M is a solubilising cation.

Sarcosinates are generally indicated by the formula

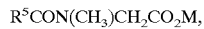

wherein R ranges from $C_8$–$C_{20}$ alkyl, preferably $C_{12}$–$C_{15}$ alkyl and M is a solubilising cation.

Taurates are generally identified by the formula

R⁵CONR⁶CH₂CH₂SO₃M, wherein $R^5$ ranges from $C_8$–$C_{20}$ alkyl, preferably $C_{12}$–$C_{15}$ alkyl, $R^6$ ranges from $C_1$–$C_4$ alkyl and M is a solubilising cation (such as those above).

Fatty acyl isethionates have the formula:

R—CO₂—CH₂CH₂—SO₃M where R is an alkyl group of 7 to 21 carbon atoms and M is a solubilising cation such as those above.

The anionic surfactant included in the composition will generally be selected to avoid harsh surfactant such as primary alkane sulphonate or alkyl benzene sulphonate. The amount, if any, of these is preferably less than 3% of the surfactants present.

Anionic surfactant may be used jointly with zwitterionic surfactant, notably betaine or sulphobetaine.

Zwitterionic surfactants for use in this invention will usually comply with an overall structural formula

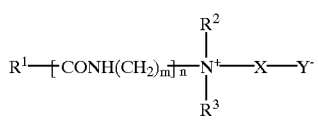

where $R^1$ is alkyl or alkenyl of 7 to 18 carbon atom
$R^2$ and $R^3$ are each independently alkyl, hydroxyalkyl or carboxyalkyl of 1 to 3 carbon atoms
m is 2 to 4
n is 0 or 1
X is alkylene of 1 to 3 carbon atoms optionally substituted with hydroxyl, and
Y is —CO₂⁻ or —SO₃⁻

Suitable zwitterionic surfactants within the above general formula include simple betaines of formula:

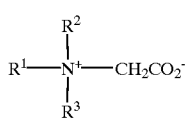

and amido betaines of formula:

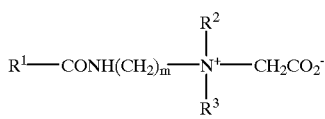

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the zwitterionic surfactant is a sulphobetaine of formula

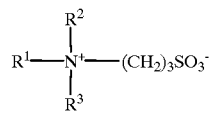

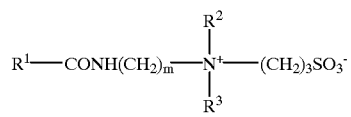

where m is 2 or 3, or variants of these in which —(CH₂)₃SO₃⁻ is replaced by

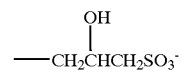

In general, the aqueous phase of the invention will comprise larger quantity of zwitterionic than anionic surfactant.

Glycoside surfactants are nonionic in character and of course includes glycoside residues. Suitably they are of the general formula:

RO(R'O)ₜ(G)ₓ or RCO₂—(R'O)ₜ(G)ₓ in which G is a residue of a pentose or hexose, R'O is an alkoxy group, x is at least unity and R is an organic hydrophobic group from 6 to 20 carbon atoms which is preferably aliphatic, either saturated or unsaturated, notably straight or branched alkyl, alkenyl, hydroxyalkyl or hydroxyalkenyl. Particularly, R may be alkyl or alkenyl of 7 to 14 or 16 carbon atoms.

The value of t in the general formulae above is preferably zero, so that the —(R'O)ₜ— unit of the general formulae is absent. In that case the general formulae become:

RO(G)ₓ or RCO₂—(G)ₓ

If t is non-zero, it is preferred that R'O is an ethylene oxide residue. Other possibilities are propylene oxide and glycerol residues. If the parameter t is non-zero so that R'O is present, the value of t (which may be an average value) will preferably lie in the range from 0.5 to 10.

The group G is typically derived from fructose, glucose, mannose, galactose, talose, gulose, allose, altrose, idose, arabinose, xylose, lyxose and/or ribose. Preferably, the G is provided substantially exclusively by glucose units. Intersaccharide bonds may be from a 1-position to a 2, 3, 4 or 6-position of the adjoining saccharide. Hydroxyl groups on sugar residues may be substituted., e.g. etherified with short alkyl chains of 1 to 4 carbon atoms. Preferably a sugar residue bears no more than one such substituent.

The value x, which is an average, is usually termed the degree of polymerization. Desirably x varies between 1 and 8. Values of x may lie between 1 and 3, especially 1 and 1.8.

Alkyl polyglycosides of formula RO(G)ₓ, i.e. a formula as given above in which t is zero, are available from Horizon Chemical Company, BASF and Henkel.

O-alkanoyl glucosides of formula RCO₂—(G)ₓ are described in International Patent Application WO 88/10147 (Novo Industri A/S). In particular the surfactants described therein are glucose esters with the acyl group attached in the 3- or 6-position such as 3-O-acyl-D-glucose or 6-O-acyl-D-glucose. Notable are 6-O-alkanoyl glucosides, in which the alkanoyl group incorporates an alkyl or alkenyl group having from 7 to 13 carbon atoms. The glucose residue may be alkylated in its 1-position with an alkyl group having from 1 to 4 carbon atoms, such as ethyl or isopropyl. Alkylation in the 1-position enables such compounds to be prepared by regiospecific enzymatic synthesis as described by Bjorkling et al. (J. Chem. Soc., Chem. Commun. 1989 p934).

Aldobionamides are amides of an aldobionic acid or aldobionolactone. Aldobionic acids are disaccharides or polysaccharides in which the aldehyde group (generally found at the $C_1$ position of the sugar) has been replaced by a carboxylic acid. Upon drying they cyclise to aldobionolactones. The disaccharide may in particular be lactose or maltose, so that the aldobionamide is a lactobionamide or maltobionamide. Further information about aldobionamides and their preparation is given in EP-A-550278.

Descriptions of alkyl polyhydroxy fatty acid amides are found in U.S. Pat. No. 2,965,576, EP 220676, EP 550557 and documents referred to therein. Polyethylene oxide-polyproylene oxide copolymers are marketed commercially, e.g. under the Trademark "Pluronic".

The foaming properties of surfactants may be evaluated by a test carried out using a panel of assessors. A suitable number of assessors to provide the panel is 20. Each panellist wears surgical gloves, turned inside out, which are first washed with soap to remove any powder eg talc from their surface and dried. Test solutions are prepared containing 2% by weight of surfactant in demineralised water. To carry out each test, 2.5 ml of a test solution is dosed slowly from a syringe directly on to the dry gloves. The panellist then rubs his or her hands together both during and after dosing the surfactant solution onto them, so as to generate a lather. The panellist takes care to avoid dropping solution from the hands. The panellist continues to generate lather by rubbing their hands together for about 10 to 20 seconds until the volume of lather is perceived as constant after which the volume of lather on the gloves is measured by the panellist submersing their hands into a bowl of water while a calibrated collecting funnel is held above them so that the lather is swept off the hands into the collecting funnel. The results obtained from each panellist are averaged.

A surfactant can be designated as a foaming surfactant if the volume of foam obtained is greater than 10 $cm^3$. An alternative definition is to state that the volume of foam for a foaming surfactant should be at least half the volume generated from sodium lauryl ethyl sulphate containing average 3 ethylene oxide residues.

A number of surfactants were tested in accordance with the above procedure and the following results were obtained.

| Surfactant mixture (2 wt % total surfactant level | Geometric mean of foam volumes/$cm^3$ |
|---|---|
| $C_{16}E_{20}$ | 3.390 |
| SLES/CAPB (13:2) | 19.303 |
| SLES | 21.500 |
| CAPB | 35.726 |
| APG | 47.705 |
| SLES/CAPBC$_{16}$E$_{20}$ (13:2:5) | 14.815 |
| SCI/CAPB | 27.667 |

In the above table $C_{16}E_{20}$ denotes C16 fatty alcohol ethoxylated with average 20 ethylene oxide residues and sold under the trade name Brij 58 by ICI.

SLES denotes soduim lauryl ether sulphate. This was Genopol ZRO containing average 3 ethylene oxide residues and supplied by Hoechst.

CAPB denotes coconut amidopropyl betaine. This was supplied as Dehyton K by Henkel.

APG denotes alkyl poly glucoside. The material used was the material supplied as Plantaren 2000 UP by Henkel. The alkyl chain has average 10 carbon atoms and the molecules contain an average of 1.4 glucoside residues.

SCI denotes sodium cocyl isethionate supplies as Jordapon CI by PPG Mazer.

Other Constituents

Other materials may be included in compositions of this invention. Possibilities include colouring agents, pearlescers, opacifying agents, proteins, glycerol and other emollients, perfumes including deodorant perfumes, buffering agents, bactericidal agents to reduce the microflora on skin, antioxidants and other preservatives.

Packaging and Dispensing

When a composition of this invention takes the form of a gel, which is not completely self-levelling, we have found it desirable to supply the composition in a pack which subjects the composition to shear at the time of use. This has the effect of making the composition appear homogenous as it is dispensed. In other words, even if the composition is somewhat lumpy in appearance within the pack, it appears smooth when dispensed from it. Such a pack may be a flexible container with a relatively small outlet orifice through which the user squeezes the composition. A suitable container is for instance in the form of a tube dimensioned so that it can be held in the hand and squeezed. The outlet orifice is generally closable and preferably has a cross sectional area in the range from 1–3 $mm^2$. A round hole of diameter 1.5 mm has been found suitable, for example.

EXAMPLE 1

In this example a number of biopolymers that is polymers of natural origin were screened for compatibility with surfactant. Compositions were prepared containing the polymers together with surfactant. The polymers which were used and their suppliers are set out in the following table:

| Material Name | Trade Name | Supplier |
|---|---|---|
| Kappa carrageenan | Genugel X0909 | Hercules |
| Iota carrageenan | Genuviso X0908 | Hercules |
| Lambda carrageenan | Genugel X-3948 | Hercules |
| LM Pectin | DE35 X3935 | Hercules |
| HM Pectin | Slendid 200 | Hercules |
| Alginate | Manucol DM | Hercules |
| Agar | Deltagar LTS | Quest |
| Gellan | Kelcogel F | Kelco |
| Glucomannan | Propol R5 | Shimizu Corporation |
| Locust Bean Gum (LBG) | Flour M-175 | Meyhall |
| Gelling starch | 77-1750 | NSCC |
| Guar | Meypro Guar | Meyhall |
| Xanthan | Keltrol F | Kelco |
| Hydroxy propyl methyl cellulose (HPMC) | HMP 450 GP 60# | Courtaulds Chemistry |
| Carboxy methyl cellulose (CMC) | 9M31 XF | Aqualon |
| Gelatin | 250 Bloom | Extraco |
| Caseinate | Spray Bland | DMV |

Two surfactants were used; sodium lauryl ether sulphate, average 3EO, (SLES) supplied by Akzo as Elfan NS 243S and coconut amidopropyl betaine (CAPB) supplied by Goldschmidt as tegobetaine CK.

The surfactants were used in a constant ratio of 13 parts SLES to 2 parts CAPB. The general method of preparation was to dissolve the surfactants in demineralised water to make up a concentrated solution (25% wt surfactant) at 60–70° C. The polymer in powdered form was dissolved in demineralised water at 90–100° C. Appropriate quantities of the two solutions were then mixed to form a solution containing 10% wt surfactant and a chosen concentration of polymer, usually 1% by wt. The mixed solution was left to cool, stored for 24–48 hours to allow gel formation to take place and then assessed visually. If a gel had formed the strength of the gel was assessed by tilting the container and/or disturbing the gel with a glass rod.

Results obtained are set out in the following table:

| Polymer | SLES/CAPB |
| --- | --- |
| 1% Kappa carrageenan | Clear, low viscosity solution, suspends air at 10%. |
| 1% Iota carrageenan | Clear gel |
| 1% Lambda carrageenan | Clear, runny solution, no gelation |
| 1% LM Pectin | Clear, runny solution, no gelation |
| 1% HM Pectin | Phase separation |
| 1% Alginate | Phase separation |
| 1% Agar | Phase separation |
| 0.5% Gellan | Phase separation |
| 0.5% Glucomannan | Phase separation |
| 0.2% LBG | Phase separation |
| 13% 97-2 Starch | Phase separation |
| 0.5% Guar | Turbid solution |
| 1% Xanthan | Turbid thickened solution |
| 1% HPMC | Clear thin solution |
| 1% CMC | Clear thin solution |
| Gelatin | Clear thin solution |
| Caseinate | Turbid solution |

EXAMPLE 2

Using Iota Carrageenan

Using the procedure of Example 1 a number of compositions were prepared containing iota carrageenan together with surfactant—which was SLES and CAPB in 13/2 ratio as in Example 1. The surfactant was used at concentrations of 5, 10 and 15% by wt. Some of the compositions contained potassium chloride electrolyte. Results obtained are set out in the following table:

| wt % surfactant | wt % KCl | Result |
| --- | --- | --- |
| 5 | 0 | Weak gel |
| 10 | 0 | Elastic gel |
| 15 | 0 | Thick, weak gel |
| 5 | 1 | Elastic gel |
| 5 | 3 | Weak gel |
| 10 | 1 | Elastic gel |
| 10 | 3 | Viscous, mobile |
| 10 | 5 | Very viscous, mobile |
| 15 | 3 | Viscous, mobile |
| 15 | 4 | Very viscous, mobile |

EXAMPLE 3

Using Kappa Carrageenan

The procedure of Example 2 was repeated using varying concentrations of kappa carrageenan and 10% surfactant (SLES and CAPB in 13:2 ratio). A viscous liquid was obtained using 1.4% kappa carrageenan, a soft gel using 1.6% kappa carrageenan and a solid gel using 1.8 and 2% kappa carrageenan.

EXAMPLE 4

Using Mixed Carrageenans

The procedure of Example 2 was repeated using 10% and varying concentrations of kappa and iota carrageenan. Results obtained are set out in the following table:

| Kappa wt % | Iota wt % | Result |
| --- | --- | --- |
| 0 | 0.6 | Elastic gel |
| 0 | 0.8 | Thick elastic gel |
| 0.8 | 0.3 | Elastic gel |
| 0.8 | 0.5 | Elastic gel |
| 1.2 | 0.2 | Thick, flowing |
| 1.2 | 0.6 | Solid gel |
| 1.2 | 1.0 | Solid gel |
| 2 | 0.2 | Solid gel |

EXAMPLE 5

Using Lambda Carrageenan

The procedure of Example 2 was repeated using 10% surfactant and various percentages of lambda carrageenan. A thickened liquid was obtained at concentrations up to 2.5% wt % carrageenan.

When mixtures of lambda carrageenan with either iota or kappa carrageenan were employed gels were obtained as set out in the following table:

| % Kappa | % Iota | % Lambda | Result |
| --- | --- | --- | --- |
| 0 | 0.1 | 1 | Weak gel |
| 0 | 0.1 | 2 | Weak gel |
| 0 | 0.2 | 1.5 | Elastic gel |
| 0 | 0.3 | 1 | Elastic gel |
| 0 | 0.3 | 2 | Elastic gel |
| 0.8 | 0 | 1 | Thick liquid |
| 0.8 | 0 | 1.2 | Thick liquid |
| 0.8 | 0 | 2 | Soft gel |
| 1.0 | 0 | 1.2 | Soft gel |
| 1.2 | 0 | 1.0 | Soft gel |
| 1.4 | 0 | 1.2 | Soft gel |

EXAMPLE 6

Using Various Surfactants

The procedure of Example 1 was repeated using 1 wt % concentration of iota carrageenan, with 10% wt of the surfactants set out in the following table:

| Material Name | Trade Name | Supplier |
| --- | --- | --- |
| Sodium Lauryl Ether (3EO) sulphate (SLES) | Elfan NS 243S | Akzo |
| Sodium Lauryl 12 EO sulphate ($SLE_{12}S$) | Standapol 125-E | Henkel |
| Coco amido propyl | Tegobetaine CK | Goldschmidt |

| Material Name | Trade Name | Supplier |
| --- | --- | --- |
| betaine (CAPB) | | |
| Alkyl poly glucoside | Plantaren 2000 | Henkel |
| Sodium cocoyl isethionate | Jordopon CIUP | PPG/Mazer |
| Disodium PEG5 lauryl citrate sulphosuccinate | Rewopol SB CS 50 | Rewo |
| Coconut acid alkylolamide sulphosuccinate | Rewopol SB 212 P | Rewo |

Thickened compositions, generally in the form of gels, were obtained in each case.

EXAMPLE 7

Assessments by Users

A number of compositions were prepared by the procedure of Example 1 containing 10% wt of surfactant (13:2 SLES:CAPB) and varying amounts of carrageenan as set out in the following table:

| % Iota | % Kappa | % Lambda |
| --- | --- | --- |
| 0.9 | 0.7 | 0 |
| 0.5 | 1.6 | 0 |
| 0.2 | 1.8 | 0 |
| 1.0 | 0 | 0 |
| 0.5 | 1.3 | 0 |
| 0.3 | 0 | 2.0 |

The gels were packed in 150 ml translucent polyethylene tubes with 1.5 mm diameter outlets.

These samples were assessed by 24 female panellists who were instructed to observe the visual appearance and flow of the products in the pack, then squeeze some of the composition from the tube onto a transparent plastic sheet and make a visual observation of the product, then feel the product with their finger tips. Subsequently they were asked to wash their forearms using each of the products. As a comparison the panellists were provided with a conventional shower gel in which aqueous surfactant was thickened by incorporation of salt.

The panellists generally commented that the products of this invention were less sticky or stringy than the control composition and that when dispensed from the tube the dispensed material was less prone to slump under its own weight. (That observation can be attributed to the strongly shear thinning character of the products of the invention). When used for washing the products of the invention were perceived as clean rinsing leaving no residue on the skin. They were observed to leave little or no residue or tackiness on the skin after drying.

We claim:

1. A thickened, aqueous detergent composition having an aqueous phase containing foaming surfactant, carrageenan and water;

wherein at least half of the carrageenan is selected from the group consisting of iota carrageenan, kappa carrageenan and mixtures thereof;

wherein said aqueous phase contains at least about 5% by wt. anionic surfactant and a lesser quantity of zwitterionic surfactant;

wherein said aqueous phase further includes electrolyte other than surfactant and wherein said electrolyte other than surfactant is selected from the group consisting of sodium ions, potassium ions, calcium ions and mixtures thereof; and wherein said foaming surfactant makes up at least two thirds of the total level of surfactant in the composition.

2. A composition according to claim 1 wherein the foaming surfactant is selected from the group consisting of anionic, nonionic, amphoteric and zwitterionic surfactants, and mixtures thereof.

3. A composition according to claim 2 wherein the aqueous phase contains at least 3 wt % anionic surfactant.

4. A composition according to claim 3 wherein the aqueous phase contains 5 to 20 wt % anionic surfactant.

5. A composition according to claim 1 wherein the foaming surfactant is selected from the group consisting of anionic, amphoteric and zwitterionic, and nonionic other than ethoxylated fatty alcohol surfactants, and mixtures thereof, and wherein the foaming surfactant makes up at least half of the total level of surfactant in the composition.

6. A composition according to claim 1 wherein the foaming surfactant contains nonionic surfactant selected from the group consisting of alkyl glycosides, O-alkanoyl glycosides, polyethylene oxide-polypropylene oxide block copolymers, alkyl polyhydroxyamides, alkyl aldobionamides and their mixtures.

7. A composition according to claim 1 to wherein the aqueous phase contains in total from 7 to 20 wt % surfactant.

8. A composition according to claim 1 wherein the aqueous phase contains from 0.05 to 5% by weight of carrageenan.

9. A composition according to claim 1 wherein the aqueous phase contains from 0.3 to 5 wt % carrageenan.

10. A composition according to claim 1 wherein the aqueous phase contains from 0.1 to 5 wt % of electrolyte other than surfactant.

11. A composition according to claim 1 wherein the composition consists solely of a thickened aqueous phase.

12. A composition according to claim 1, wherein the composition has incorporated solid or liquid suspended particles.

13. A pack containing a composition according claim 1, which pack subjects the composition to shear as it is dispensed therefrom so as to give the dispensed composition a smooth appearance.

14. A pack containing a composition according to claim 1 which is a flexible container having a closable outlet orifice with a diameter of 1–3 mm$^2$ cross section.

* * * * *